US008961615B2

(12) United States Patent
Rogachefsky

(10) Patent No.: US 8,961,615 B2
(45) Date of Patent: Feb. 24, 2015

(54) BONE PROSTHESIS FOR MAINTAINING JOINT OPERATION IN COMPLEX JOINTS

(71) Applicant: Richard A. Rogachefsky, Torrance, CA (US)

(72) Inventor: Richard A. Rogachefsky, Torrance, CA (US)

( * ) Notice: Subject to any disclaimer, the term of this patent is extended or adjusted under 35 U.S.C. 154(b) by 0 days.

(21) Appl. No.: 14/320,684

(22) Filed: Jul. 1, 2014

(65) Prior Publication Data
US 2014/0316529 A1 Oct. 23, 2014

Related U.S. Application Data

(62) Division of application No. 13/731,160, filed on Dec. 31, 2012, now Pat. No. 8,801,796.

(51) Int. Cl.
*A61F 2/30* (2006.01)
*A61F 2/42* (2006.01)

(52) U.S. Cl.
CPC ........... *A61F 2/4261* (2013.01); *A61F 2/30721* (2013.01); *A61F 2/4202* (2013.01); *A61F 2002/30079* (2013.01); *A61F 2210/009* (2013.01); *A61F 2002/4289* (2013.01)
USPC .................. 623/21.14; 623/18.12; 623/21.18

(58) Field of Classification Search
CPC .............. A61F 2002/4289; A61F 2002/30079; A61F 2210/009; A61F 2/4261; A61F 2002/4261
USPC ....................... 623/18.11, 21.11–21.14, 18.12
See application file for complete search history.

(56) References Cited

U.S. PATENT DOCUMENTS

| | | | |
|---|---|---|---|
| 4,024,588 A | 5/1977 | Janssen et al. |
| 4,164,793 A | 8/1979 | Swanson |
| 4,198,712 A | 4/1980 | Swanson |
| 4,216,548 A | 8/1980 | Kraus |
| 4,936,860 A | 6/1990 | Swanson |
| 5,879,386 A | 3/1999 | Jore |
| 5,888,203 A | 3/1999 | Goldberg |
| 6,245,109 B1 | 6/2001 | Mendes et al. |
| 6,716,249 B2 | 4/2004 | Hyde |
| 2002/0111690 A1 | 8/2002 | Hyde |
| 2002/0128651 A1 | 9/2002 | Hyde, Jr. |
| 2003/0236572 A1 | 12/2003 | Bertram |
| 2004/0138754 A1 | 7/2004 | Lang et al. |
| 2006/0142865 A1 | 6/2006 | Hyde, Jr. |
| 2007/0100457 A1 | 5/2007 | Hyde, Jr. |
| 2008/0306324 A1 | 12/2008 | Bonutti et al. |
| 2011/0066245 A1 | 3/2011 | Lang et al. |
| 2011/0257754 A1 | 10/2011 | Fleischmann |

OTHER PUBLICATIONS

KIPO International Search Report and Written Opinion of the International Searching Authority in corresponding International Application No. PCT/US2013/078272 completed Apr. 2, 2014 (16 pages).

*Primary Examiner* — David H Willse
*Assistant Examiner* — Javier Blanco
(74) *Attorney, Agent, or Firm* — Brian B. Shaw, Esq.; Andrew J. Anderson, Esq.; Harter Secrest & Emery LLP

(57) ABSTRACT

A prosthesis for reconstructing a multibone joint such as a wrist. A patient's scaphoid is removed to create a void. The scaphoid has a plurality of adjacent bones, each of the adjacent bones comprising a surface generally facing the void. The surface of at least two of the adjacent bones is prepared by affixing a magnetic element thereto and a magnetic scaphoid implant is inserted into the void. A magnetic relationship exists between the magnetic elements and the magnetic scaphoid implant.

12 Claims, 8 Drawing Sheets

BONE PROSTHESIS FOR MAINTAINING JOINT OPERATION IN COMPLEX JOINTS

CROSS-REFERENCE TO RELATED APPLICATIONS

This application is a divisional of prior filed U.S. patent application Ser. No. 13/731,160 filed Dec. 31, 2012, now the U.S. Pat. No. 8,801,796, the disclosure of which is incorporated by reference herein.

FIELD OF THE INVENTION

This invention relates generally to joint repairs and replacements. More specifically, this invention relates to repairing a wrist by replacing a bone proximate the joint with a prosthetic including a magnet.

BACKGROUND OF THE INVENTION

As is conventionally known, the wrist is a very intricate interconnection of several bones, ligaments and tendons. The cooperation of these results in an elegant system allowing for varied and complex movement. FIG. 1 shows the conventional structure, which includes five metacarpals 2, the radius 4, the ulna 6, and eight carpal bones. The carpal bones include the trapezium 10, the trapezoid 12, the capitate 14, the hamate 16, the pisiform 18, the triquetrum 20, the lunate 22, and the scaphoid 24.

As illustrated in FIG. 1, outer surfaces of the scaphoid 24 cooperate with corresponding surfaces of the surrounding carpal bones and the radius.

Arthritis of the wrist is a common ailment. There are multiple etiologies for the development of wrist degenerative arthritis, including trauma, inflammatory, and crystal induced. The two most common causes of wrist degenerative arthritis are scapholunate ligament tears and scaphoid fractures. When a scapholunate ligament tear is left untreated, a progression of degenerative arthritis can occur, known as SLAC wrist. Scaphoid fractures that do not heal and that go onto non-union develop a progression of wrist degenerative arthritis known as SNAC wrist.

In SLAC wrist, the progression of the degenerative arthritis originates at the radial styloid. Due to the abnormal mechanics after a scapholunate ligament tear, the main stabilizer between the scaphoid and lunate is disrupted. As a result, the scaphoid flexes forward and the lunate and triquetrum extend dorsally. Due to the fact that the scaphoid is volar flexed it has difficulty clearing the radial styloid with wrist flexion and extension, causing abnormal wear and degeneration at the radial styloid. This is the first stage of SLAC wrist degenerative arthritis.

The second stage occurs with increased abnormal mechanics at the radioscaphoid joint region. As a result of the scaphoid being in a more flexed position, increased pressure and wear occur on the dorsal aspect of the scaphoid fossa articular surface of the distal radius and dorsal aspect of the scaphoid. With continued abnormal forces and wear, formation of degenerative arthritis occurs. In the third stage, the arthritis occurs at the capitolunate joint, and stage four occurs when the capitate head sinks deeper in the interval between the scaphoid and lunate. In many cases the radiolunate joint is spared, but not always.

In stage 1 of SNAC wrist, the distal pole of the scaphoid cannot clear the radial styloid and degenerative arthritis occurs at the styloid region. In stage 2, degenerative arthritis occurs at the radioscaphoid joint. In stage 3 the arthritis occurs at the capitolunate joint.

In both types, the disease progression is fairly predictable. Conventional attempts at combatting arthritis at any stage generally include reconstructive procedures such as removing carpal bones and/or fusing several of the carpal bones to each other as well as to the radius. These types of drastic procedure can severely limit motion of the wrist after surgery.

Accordingly, there is a need in the art for an improved method and procedure for repairing the wrist.

As a result there is a need for a procedure that can recreate the normal anatomic relationship of the carpal bones, can recreate the normal anatomy and kinematics of the wrist in the earlier stages of the disease, and will lead to improved functional outcomes as compared to the reconstructive procedures that are used presently. To this end, there also is a need in the art for a procedure for replacing the scaphoid while maintaining relative movement of the carpal bones relative to each other as well as relative to the radius and ulna.

SUMMARY OF THE INVENTION

This disclosure satisfies the foregoing need in the art by providing an improved method and apparatus for doing selective replacement of portions of the wrist, including replacing only the scaphoid.

In one aspect of the invention, a method of reconstructing a wrist includes removing a patient's scaphoid to create a void. The scaphoid has a plurality of surfaces and a plurality of adjacent bones that are aligned with the scaphoid surfaces, each of the adjacent bones comprising a joint surface generally facing the void. The joint surfaces of at least two of the adjacent bones are prepared by affixing a magnetic element to the bone, and a scaphoid implant is inserted into the void. A magnetic relationship exists between the magnetic element(s) and the scaphoid implant. More specifically, the magnetic element(s) and/or the scaphoid implant include a magnet.

In another aspect of the invention, a prosthesis includes a magnetic implant approximating the size of a bone to be replaced; a first magnetic bone implant securable to a first bone adjacent the bone to be replaced; and a second magnetic bone implant securable to a second bone adjacent the bone to be replaced, wherein each of the first and second magnetic bone implants have a magnetic relationship with the magnetic implant.

In another aspect of the invention, a prosthesis includes a scaphoid implant approximating the size of a scaphoid to be replaced, a first bone implant securable to a first bone adjacent the scaphoid to be replaced, and a second bone implant securable to a second bone adjacent the scaphoid to be replaced. The first and second bone implants each have a magnetic relationship with the scaphoid implant.

In another embodiment of the invention as more joint surfaces are effected by the disease process more magnetic connections are necessary.

These and other aspects and features of the invention will be appreciated with reference to the following detailed description and accompanying figures, in which preferred embodiments of the invention are described and illustrated.

BRIEF DESCRIPTION OF THE SEVERAL VIEWS OF THE DRAWING(S)

DETAILED DESCRIPTION OF THE INVENTION

As noted above, the present invention relates to joint replacement. One present embodiment of the invention will be described with reference to FIG. 2.

As used herein, a "magnetic element" generally refers to a component that includes a magnet or that responds to a magnetic field, i.e., by being attracted to or repelled by a magnet.

A "magnetic implant" is a type of magnetic element that is implanted into the body.

Figure 1:
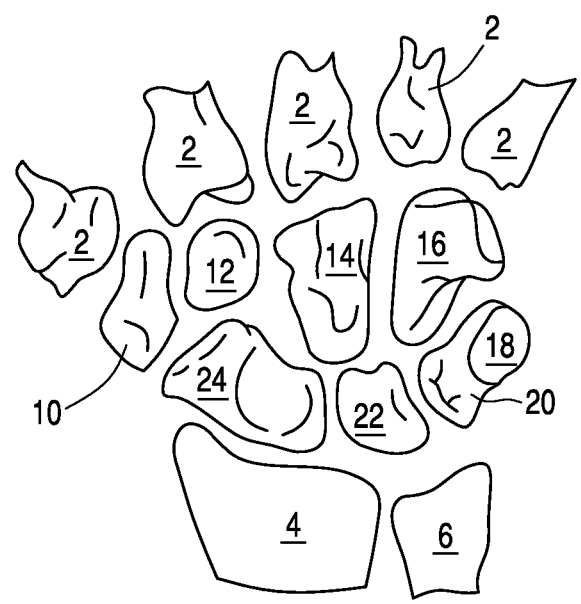
FIG. 1 is perspective view showing the anatomy of the human wrist.
Figure 2:
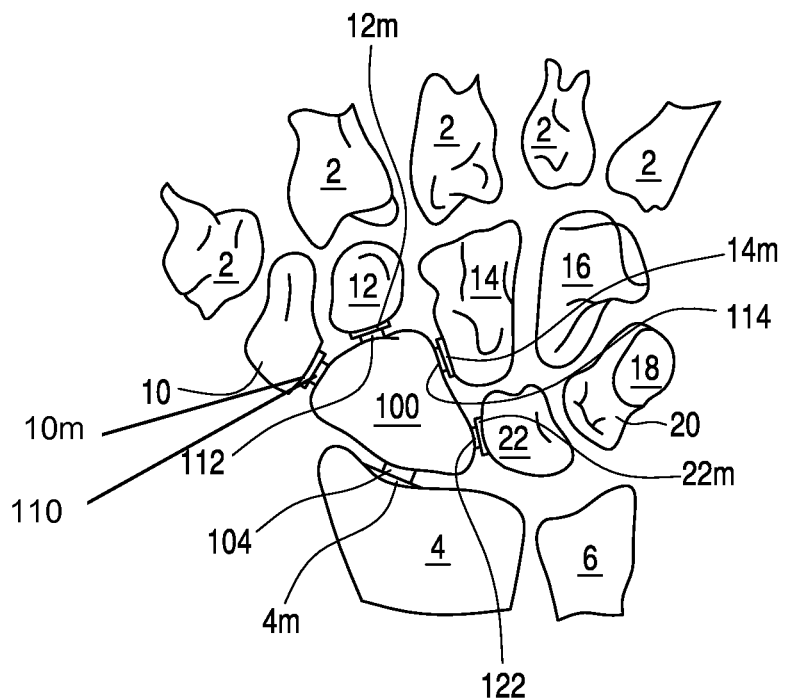
FIG. 2 is a perspective view of a preferred embodiment of a wrist-repair apparatus according to this disclosure, in which a prosthesis replaces the scaphoid.

In FIG. 2, the bones of the wrist are illustrated. Specifically, the metacarpal bones 2, the radius 4 and seven of the carpal bones 10, 12, 14, 16, 18, 20, 22 are illustrated. Different from the natural anatomy of the hand, however, the scaphoid has been removed from the hand illustrated in FIG. 2. In its place, a magnetic implant, here a scaphoid implant 100 has been inserted such that the implant 100 is aligned proximate to the adjacent bones. The implant 100 is illustrated as having a generally oblong shape, substantially similar to the shape of the removed scaphoid. Accordingly, the implant 100 is arranged proximate surfaces of the trapezium 10, the trapezoid 12, the capitate 14, the lunate 22 and the radius 4.

In the embodiment of FIG. 2, the implant 100 features a series of scaphoid implant magnetic elements 110, 112, 114, 122, 104 disposed on an external surface of the scaphoid implant 100. In the illustrated embodiment, each of the magnetic elements is a magnet arranged to face one of the bones proximate the implant 100.

The scaphoid implant magnetic elements 110, 112, 114, 122, 104 cooperate with magnetic elements disposed on each of the adjacent bones. Specifically, the scaphoid implant magnetic element 110 is arranged to cooperate with trapezium magnetic element 10m disposed on the trapezium 10, the scaphoid implant magnetic element 112 is disposed to cooperate with a trapezoid magnetic element 12m, which is disposed on the trapezoid 12, the scaphoid implant magnetic element 114 is disposed to cooperate with a capitate magnetic element 14m disposed on the capitate 14, the scaphoid implant magnetic element 122 is disposed to cooperate with a lunate magnetic element 22m disposed on the lunate 22, and the scaphoid implant magnetic element 104 is disposed to cooperate with the radius magnetic element 4m disposed on the radius 4. Each of the scaphoid implant magnetic elements 110, 112, 114, 122, 104 is illustrated as protruding from a surface of the implant 100. This is not required. For example, the magnetic elements may be imbedded in a surface of the implant 100. In one example, the implant 100 may include a series of bores or similar cutouts in its surface, each disposed to accept the respective magnetic element. The magnetic elements may be retained in such a bore or opening using any conventional method, including but not limited to adhesive, press fit, and by other mechanical fasteners.

The trapezium magnetic element 10m, the trapezoid magnetic element 12m, the capitate magnetic element 14m, the lunate magnetic element 22m, and the radius magnetic element 4m all are illustrated as protruding from a surface of the respective bone to which they are attached. In practice, the magnetic elements could be attached to the bone using any known method including adhesive or mechanical fastener, cement or screw. In addition in another embodiment the magnets could be flush with the surface of the respective bone. As will be appreciated by those of ordinary skill in the art, the surface of the respective bone to which each of the magnetic elements is placed may require some preparation prior to attachment of the magnetic element. For example, each of the bone surfaces to which the magnetic elements are attached may need to be stripped of any ligament. Moreover, degenerated cartilage and bone material may necessarily be removed from the bone.

As indicated above, the magnetic implants disposed on the carpal bones surrounding the removed scaphoid and the magnets disposed on the scaphoid magnetic implant cooperate with each other. Accordingly, they are provided in a one-to-one correspondence, i.e., each magnetic element in each carpal bone has a mating or coupling magnetic surface in the scaphoid magnetic implant. In one embodiment, both magnetic elements in each of the respective couplings include magnets, which cooperate by having an opposite polarity, thus attracting each other. In this embodiment, an attraction is made between the trapezium magnetic element 10m and the scaphoid implant magnet 110, the trapezoid magnetic element 12m and the scaphoid implant magnet 112, the capitate magnetic element 14m and the scaphoid implant magnet 114, the lunate magnetic element 22m and the scaphoid implant magnet 122, and the radial magnetic element 4m and the scaphoid implant magnet 104. Each of the scaphoid implant magnets may have a north polarity while the bone magnetic elements disposed on the carpal bones and the radius will have a south pole. Of course, this arrangement could be reversed. Moreover, some of the implant magnets could have a north polarity while others have a south polarity. The respective coupling carpal bone or radius magnetic elements have the opposite polarity in this arrangement.

In still other embodiments of the invention, it may be desirable that the respective implant and bone magnet couples repel each other. In one such embodiment, the scaphoid implant 100 would be repelled by the magnetic elements associated with each of the carpal bones 10, 12, 14, 22 and the radius 4, causing the scaphoid implant to remain suspended between each of the bones. In other arrangements, some scaphoid implant/bone magnet couples could attract while others could repel.

According to the embodiments just described, the functionality of the wrist after inserting the implant 100 is substantially the same as prior to surgery and removal of the scaphoid. The magnet pairs preferably, whether attracted or repelled relative to each other, will move relative to each other in a sliding engagement, as necessary, recreating the normal kinematics of the wrist. Thus, the drawbacks of a complete wrist fusion are avoided, but the defective scaphoid and degenerative surfaces of the adjacent bones are removed, thereby providing pain relief and increased function.

Although FIG. 2 shows five magnet pairs, other embodiments also are contemplated. For example as few as two magnet pairs could be included. In preferred embodiments, those pairs could include the implant magnet 112 and the trapezoid magnet 12m and the implant magnet 104 and radius magnet 4m. Similarly, the pairs may be the implant magnet 110 and the trapezium magnet 10m and implant magnet 122 and lunate magnet 22m. In each of these alternative embodiments, the magnet pairs may preferably be disposed proximate opposite sides of the scaphoid implant 100, although such is not necessary. The magnet pairs may instead be disposed on adjacent bones such as on the lunate and the capitate, by way of non-limiting example.

In accordance with another alternative embodiment of the invention, the implant magnets 110, 112, 114, 122, 104 or the magnetic elements attached to the bones 10m, 12m, 14m, 22m, 4m may not be magnets at all. Instead, one or the other could be a ferrous material or an alternative material that responds to a magnetic field so as to be attracted (or repelled) by the magnet disposed on the adjacent surface. For example, each of the implant magnets 110, 112, 114, 122, 104 could be a ferrous material instead of a magnet, and thus would be attracted to each of the magnets disposed on the carpal bones and the radius. In a similar embodiment, the implant 100 may simply be made of a ferrous material, which would be attracted to the magnets disposed on the bones. This arrangement would alleviate the need for separate components attached to the implant 100, such as those surfaces illustrated by reference numerals 110, 112, 114, 122, and 104. Although adjacent surfaces of the bone and the magnetic material are shown as being generally planar, this is not required. For example, the magnets may have surface curvature which may approximate the curvature of the scaphoid and/or other, adjacent bones.

In yet another embodiment of the invention, the scaphoid implant 100 may be a magnet, and the bone magnetic elements represented by reference numerals 10m, 12m, 14m, 22m, and 4m may be ferrous surfaces or magnets of opposite polarity. The ferrous surfaces may be implanted, or may simply be added to a screw or the like that is fastened to the bone. In this embodiment, the implant 100 will attract each of the implants placed in the proximate bones, resulting in a similar arrangement as described above.

Depending upon the strength of the magnets used, the embodiments of the invention may further require a shield that is placed over the magnetic components of the invention, i.e., to limit the impact of the magnetic field beyond the inside of the wrist. For example, it may be desirable to shield the magnetic components to prevent accidental attraction or repulsion of the magnetic components to metal or magnets in the environment that the user may operate or handle with the hand having the replaced wrist.

A preferred method of using an implant 100 such as described above generally includes making an incision in the user's wrist. This is common with a conventional wrist replacement surgery. The scaphoid preferably is freed from adjacent bones and tissue by cutting connective tissue, and is then removed from the wrist entirely. The surfaces of the trapezium 10, trapezoid 12, capitate 14, lunate 22 and the radius 4 that articulate with the scaphoid are then prepared by removing any connective tissue and degenerated cartilage and bone, as appropriate.

An implant or a component is then fixed to each of those prepared surfaces. For example, the implant may be the bone magnetic elements 10m, 12m, 14m, 22m, and 4m described above. As noted above, the magnets may be fixed to the surface of the bones by any conventional means including adhesive and mechanical fasteners, such as bone cement. In one embodiment, the magnet is arranged on the head of a screw, such as a surgical screw, which would be inserted into the bone in a conventional manner by a surgeon. Once each of the surfaces has been prepared, the scaphoid implant 100 is put into place between those surfaces. The scaphoid implant 100 may be sized such that it is pressed into the opening between the prepared surfaces with force. Once pressed into place, the magnetic relationship between the scaphoid implant magnetic elements 110, 112, 114, 122 and 104 and the bone magnetic elements 10m, 12m, 14m, 22m, and 4m act to retain the scaphoid implant 100 in place. As required, a shielding mechanism may be placed over the magnets. The shield is so placed to shield the magnetic field from affecting any area outside of the wrist. In one embodiment, the magnets and the shielding mechanism may be integrally formed. For example, the magnets may be generally cylindrical in shape, with a center, cylindrical region that is magnetized and a surrounding cylindrical region that is non-magnetized. This non-magnetized region could actually act to dissipate the magnetic field of the central magnet, so the magnetic field acts substantially only at the ends of the magnet. The procedure is completed by suturing the incision closed.

Figure 3:
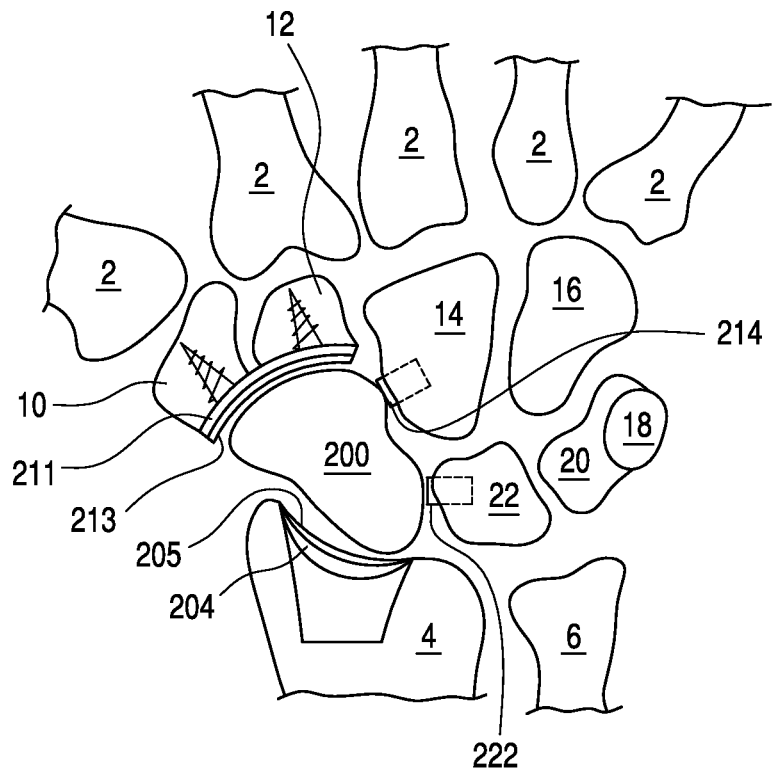
FIG. 3 is a perspective view of another preferred embodiment of a wrist-repair apparatus according to this disclosure.

Another embodiment of the invention is illustrated in FIG. 3, in which a single magnetic element is included as a plate 211, spanning and attached to both the trapezium 10 and the trapezoid 12. As illustrated by this embodiment, it is not required that the magnetic bone implants and the bones have a one-to-one correspondence as in the prior embodiments, but instead a single magnetic implant may be fixed to more than one bone. In this embodiment, the scaphoid implant 200 is magnetic and the magnetic bone implant 211 spanning the trapezium 10 and the trapezoid 12 has an opposite polarity, such that the magnetic bone implant 211 is attracted to the scaphoid implant 200.

Also in this embodiment, an insert 213 is fastened to the magnetic bone implant 211 such that the insert 213 is arranged on a face of the bone implant 211 facing the scaphoid implant 200. The insert 213 is disposed for contact by the scaphoid implant 200, and provides a surface upon which the implant 200 moves freely. In a preferred embodiment, the insert 213 is made of a biocompatible material having a low coefficient of friction. Examples of such materials include polymers such as polyethylene, ceramics, and pyrolytic carbon (pyrocarbon). The insert 213 is preferably to provide a smooth gliding surface to prevent metal-on-metal wear, especially because the opposing implant contact surfaces will move relative to each other. Also the insert will be thin enough and be made of appropriate material to allow unimpeded attraction of magnetic surfaces on opposing sides of the insert 213.

The implant 213 preferably is fixed to the magnetic bone implant 211. Fasteners may be used to this end, but in a preferred embodiment the insert is sized to be snapped onto the magnetic bone implant 211. In one embodiment, edges of the insert have one or more extensions that engage over the sides of the bone implant 211. In another embodiment, the bone implant has one or more bores drilled therein and the insert has mating protrusions on the surface facing the bone implant 211. The protrusions are press fit into the bores to retain the insert 213 on the implant 211. Those of ordinary skill in the art will appreciate additional mechanisms for retaining the insert 213 on the implant 211.

The insert 213 preferably is contoured to accommodate the contour of the scaphoid implant 200, i.e., such that the scaphoid implant 200 and the insert 213 articulate relative to each, as in normal wrist operation. Moreover, and as will be described in more detail below, the bone implant 211 and insert 213 preferably are positioned to closely approximate the pre-surgery size and shape of the trapezium and trapezoid original surfaces.

Also illustrated in FIG. 3 is a second magnetic implant 204, provided on the distal radius 4, and having the same polarity as the first magnetic bone implant 211 spanning the trapezium 10 and the trapezoid 12. The second magnetic bone implant 204 preferably is inserted into the distal radius and an insert 205 is disposed thereon, much like the insert 213 described above. Also shown in FIG. 3 are magnetic implants, which are illustrated as substantially cylindrical magnets 214 and 222 disposed on the capitate 14 and the lunate 22, respectively. Fixation methods such as those described above may be used to affix the magnets to the respective bones. For example, the first magnetic implant 211 is screwed into the trapezium 10 and the trapezoid 12 in the illustration using surgical screws 230. The second magnetic bone implant 204 may be press fit into a cup or indentation formed in the distal radius 4, or it could be affixed using screws, adhesives or any other known method.

A preferred method of implementing the prosthetic system of FIG. 3 now will be described with reference to FIGS. 4A-4I.

Figure 4A:
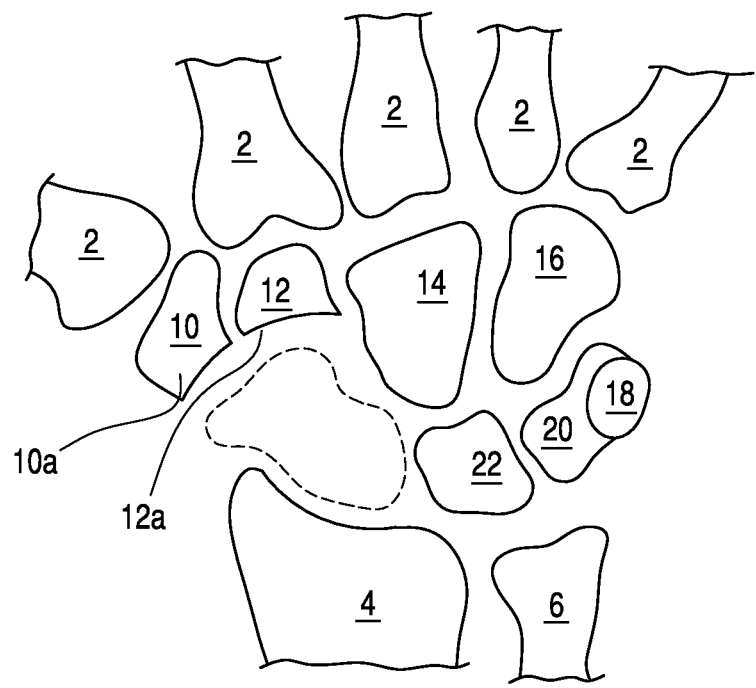
FIGS. 4A-4I illustrate a method of repairing a wrist using the apparatus illustrated in FIG. 3.

As illustrated in FIG. 4A, the defective scaphoid is first removed. As will be appreciated by those having ordinary skill in the art, the scaphoid is accessed by making necessary incisions, opening the wrist capsule, and removing ligaments, as required. As also illustrated in FIG. 4A, the surfaces 10a, 12a of the trapezium 10 and the trapezoid 12 that articulate relative to the scaphoid are precisely prepared by removing any and all arthritic bone and cartilage, using conventional tools, such as surgical saws, chisels, and the like. Jigs also may be constructed particularly for use in the method. A small amount of subchondral bone also is removed, but much of the trapezium 10 and the trapezoid 12 are left in place.

Figure 4B:
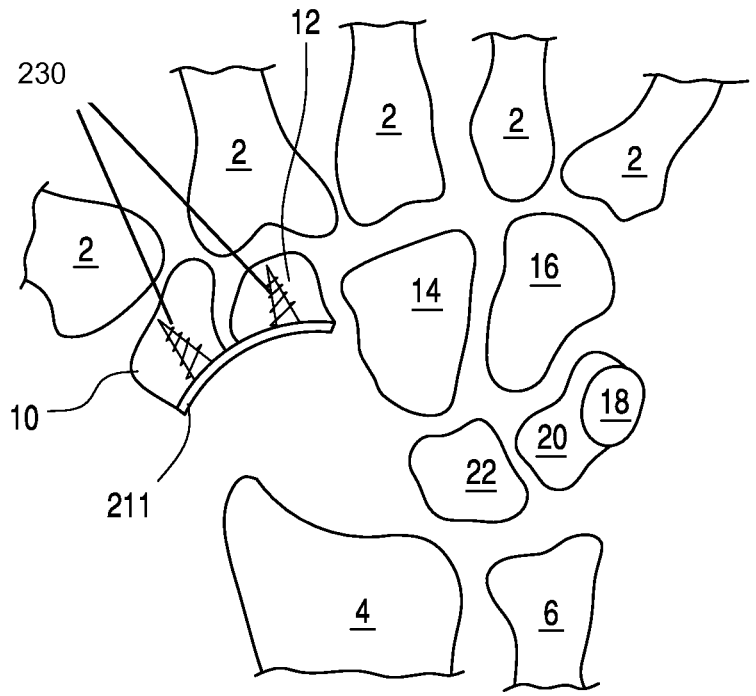

As illustrated in FIG. 4B, the first magnetic bone implant 211 is fixed to the prepared trapezium 10 and the trapezoid 12. In the illustration, surgical screws 230 are used to retain the plate 211. The screws 230 are illustrated as extending into the trapezium 10 and the trapezoid 12. In other embodiments, the screws may extend into the metacarpals, which may increase stability. Alternatively, or in addition, cement or glue may be used to fix the first magnetic bone implant 211. The surface of the implant 211 contacting the trapezium and the trapezoid preferably has bone ingrowth surfaces, as are conventional in the art.

Figure 4C:
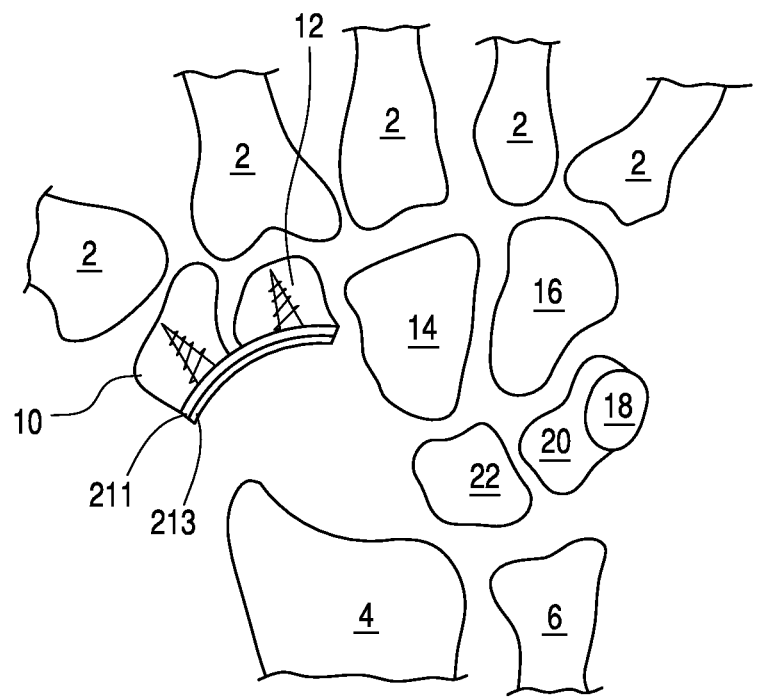

In FIG. 4C, the insert 213 is fixed to the first magnetic bone implant. As detailed above, the insert is preferably a thin, low-friction material upon which a scaphoid implant 200 will freely articulate. The insert 213 may be contoured to accommodate the scaphoid implant 200.

Figure 4D:
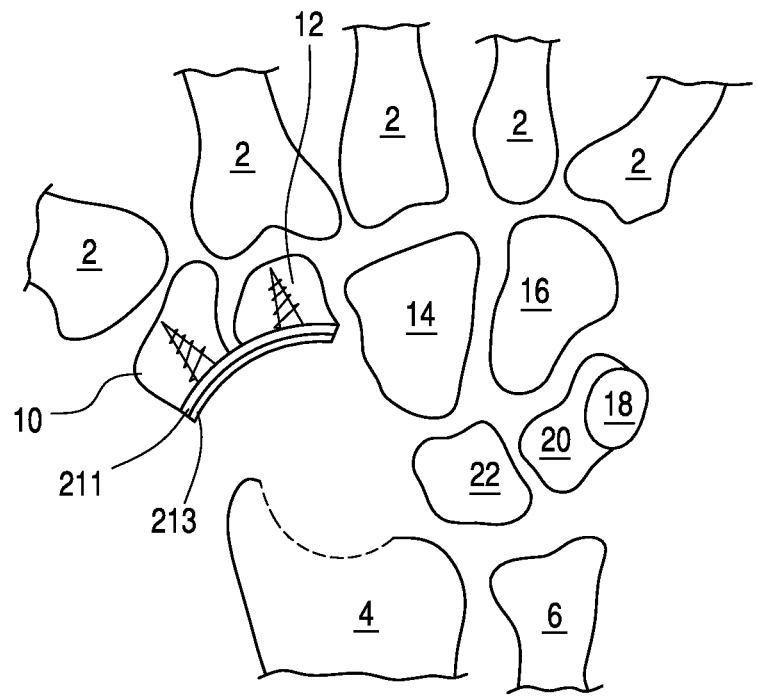

In FIG. 4D, the surgeon removes any arthritis from the portion of the radius surface that articulates with the scaphoid, namely, the radial scaphoid fossa, as well as a small amount of subchondral bone. After prepared, the radial fossa preferably has a concave shape. A bore hole (not shown) also may be drilled longitudinally into the radial fossa. The bore may be provided, to receive a spike, keel or similar protrusion on the second magnetic bone implant 204. In other embodiments, the spike or keel may be driven directly into the bone.

Figure 4E:
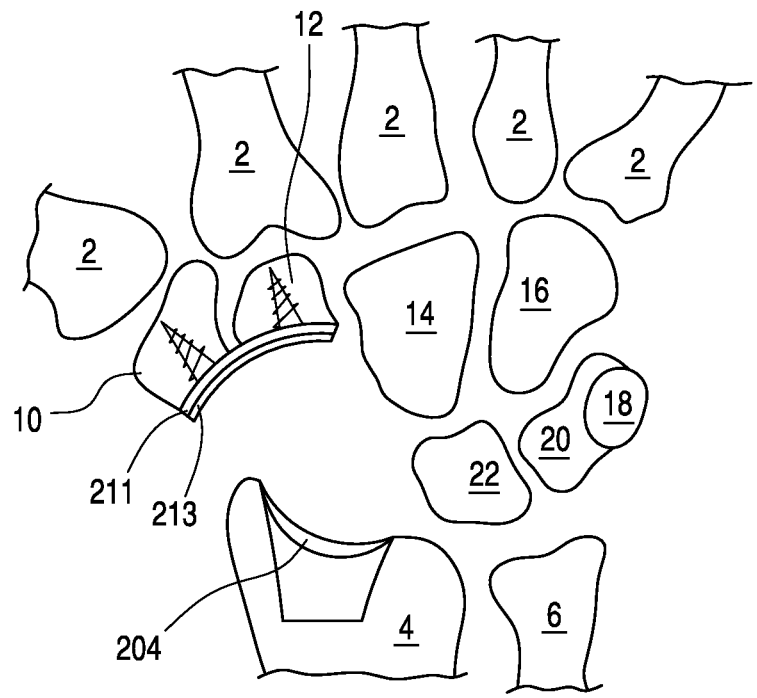

In FIG. 4E, the second bone implant 204 is fixed to the prepared surface of the radial fossa. The implant 204 may be fixed with screws, adhesive, cement, or press fit or any known methodology. In the illustrated embodiment, a keel protrudes from the back surface of the second magnetic bone implant 204 and the implant 204 is hammered into the radius. The keel provides increased fixation and stability to the implant. In other embodiments, other fasteners, such as screws, may be used for secure affixation.

Figure 4F:
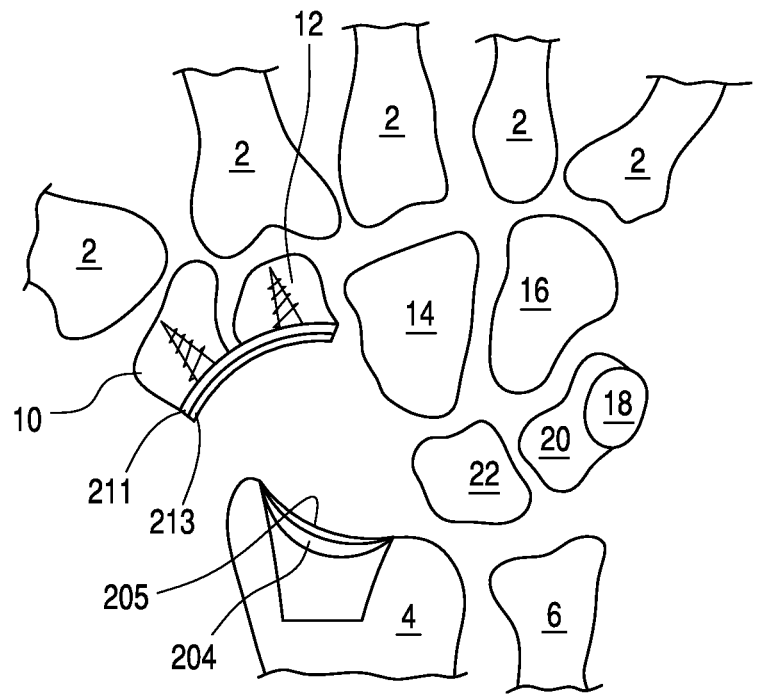

In FIG. 4F, the insert 205 is fixed to the second magnetic bone implant 204. As with the insert 213, the insert 205 preferably snaps onto the implant 204, although other attachment means may be used. Also as with the insert 213, the radial implant insert is made of a material such as polyethelene or ceramic to provide a smooth gliding surface between the implants.

Figure 4G:
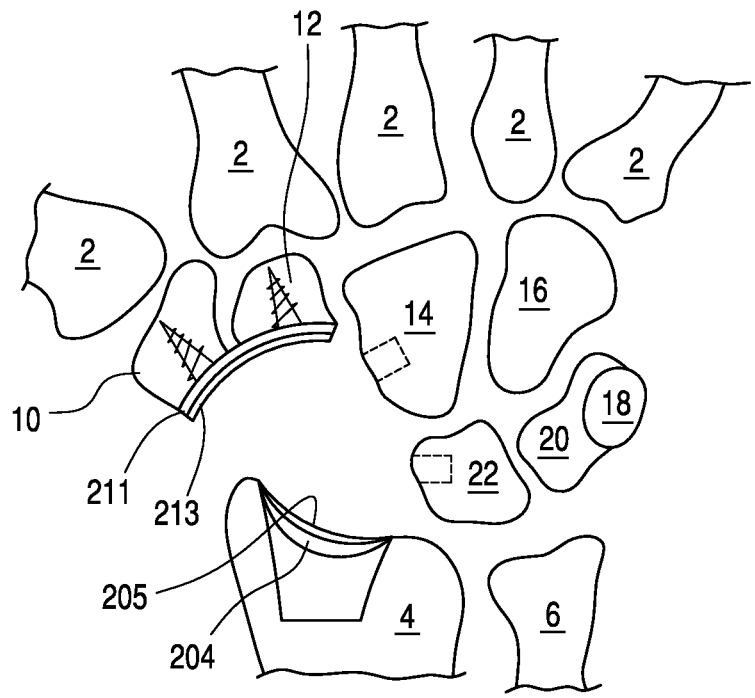
Figure 4H:
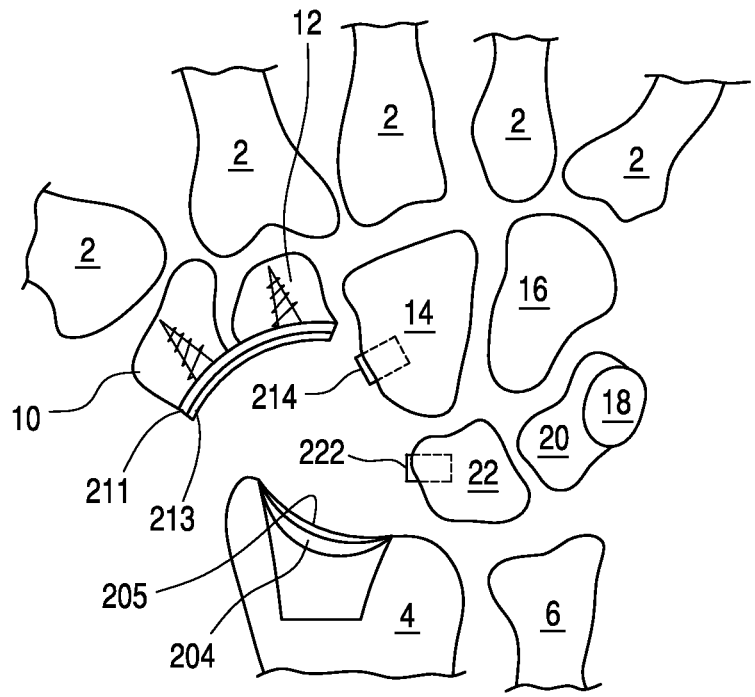

Next, as shown in FIG. 4G, the surgeon drills bore holes into the capitate 14 and the lunate 22, and in FIG. 4H the magnets 214, 222 are pressed into the bores. The magnets 214, 222 preferably are press fit into the bore holes, although they may be retained in the capitate 14 and lunate 22 by any conventional means. As with the first magnetic bone implant 211 and the second magnetic bone implant 204, the magnets 214, 222 preferably include porous ingrowth surfaces. An insert (not shown) also may be provided on each of the magnets 214, 222, to minimize friction between the magnets 214, 222 and the implant 200 (shown in FIG. 4I). Such an insert could be similar to the inserts 205, 213.

Figure 4I:
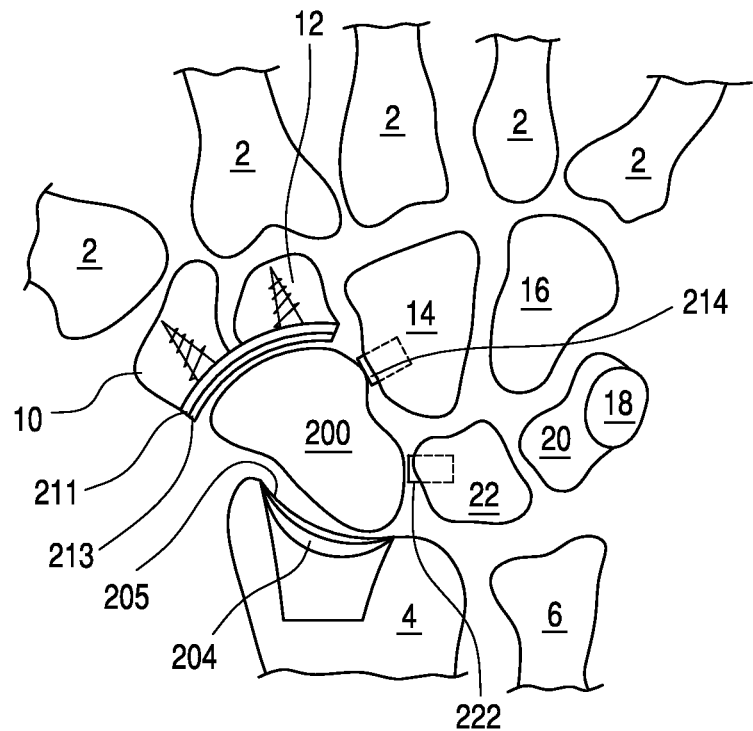

In FIG. 4I, the scaphoid implant 200 is placed in the void bounded by the inserts 205, 213. In the preferred embodiments, the surfaces of the inserts 205, 213 and of the magnets 214, 222 form a void for receiving the scaphoid implant 200. Each of those surfaces is disposed approximately at the position of the removed surface of the original bone and preferably has a concave surface. Moreover, as illustrated, the majority of the original surfaces of the lunate and capitate that face the scaphoid and in which the magnets 214, 222 are placed, are maintained, because the disease process generally will not affect those surfaces. For instance, the surface of the insert 205 approximates the position, contour and size of the original radius surface. Accordingly, the scaphoid implant 200 approximates the size and shape of the removed scaphoid (pre-injury). In this manner, the reconstructed anatomy of the wrist is substantially the same as the original anatomy of the wrist. In one preferred embodiment, the scaphoid implant is placed into the void to cooperate with recessed or concave areas of the magnets/implants placed in the trapezium, trapezoid, and radius, for example. To this end, those surfaces may have a generally concave shape to receive a generally convex feature on the outer surface of the scaphoid implant. This relationship between the concave and convex surfaces, combined with the attractive forces between the magnetic implant 200 and the magnetic implants 211, 204 and magnets 214, 222, hold the implant in place. The surgery is completed by closing up any incisions. As will be appreciated, the size and features of the implants, magnets and plates, including the convex and concave shapes of the implant and the plates fixed to the bones, are intended to closely recreate the original physiology and functioning of the wrist.

In the embodiment described in connection with FIGS. 3 and 4A-4I, the bone implants 211, 204 are magnets. That is, they may be a magnetized plate. Alternatively, the implants may be made of more than one component, for example, a non-ferrous plate or component with one or more attached magnets. The non-ferrous material may be non-metallic, such as, pyrocarbon or ceramic, which could alleviate the need for an insert, i.e., because there would be minimal friction between the implant and the scaphoid implant 200. In other embodiments, the insert may still be used. Moreover, although in the embodiments described above the insert is applied to the magnetic implants after those implants are affixed to the bone, the inserts could be applied to the magnets before the magnets are attached to the respective bones.

The magnets described in this disclosure preferably have up to 5000 Gauss surface strength. They are made from any number of materials, including neodymium, metal alloy, ceramic or rubberized magnetic material. The inserts are preferably relatively thin members, such that they do not impede the magnetic attraction between the implant 200 and the surrounding magnets/implants.

FIGS. 3 and 4A-4I generally illustrate a methodology for replacing a scaphoid in a manner that closely approximates pre-injury wrist kinematics and physiology. According to the methods described above, injured bone and/or tissue are replaced, but the remainder of the wrist is left intact. In a preferred embodiment, as much as possible of the original wrist structure is left in place. This methodology is in stark contrast to previous methods in which an entire row or more of carpal bones are removed and remaining structure is fused.

Figure 5:
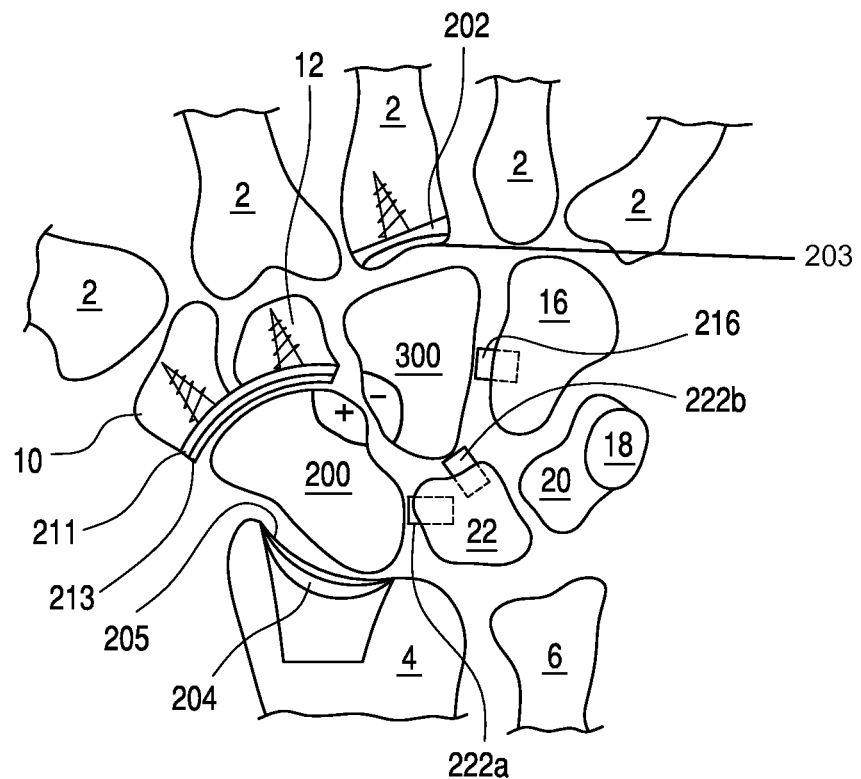
FIG. 5 is a perspective view of yet another preferred embodiment of a wrist-repair apparatus according to this disclosure.

However, the invention is not limited to replacing only the scaphoid. As described in the Background of the Invention section, common wrist arthritis diseases follow a common pattern. The embodiments described above are generally successful at repairing a SLAC or SNAC wrist that is at Stage 1 and even Stage 2. Further progressed arthritis, though, may not be fixed by replacing only the scaphoid. If the injury is not diagnosed until farther along in the process, the composition of the capitate may also be compromised. In such a situation, another embodiment of the invention contemplates providing a capitate implant, such as is illustrated in FIG. 5. It is at the discretion of the surgeon whether such an additional implant is indicated based on the severity of the disease process.

In FIG. 5, the scaphoid and capitate have been replaced, respectively, with a scaphoid implant 200 and a capitate implant 300. Like in previous embodiments, the bones surrounding those implants are prepared, e.g., by removing diseased surfaces, and bone magnetic elements are attached thereto. The scaphoid and capitate implants 200, 300 are then inserted into the respective voids created by removing the native bones. In a preferred embodiment, the scaphoid and capitate implants 200, 300 are attracted to each other, as is generally illustrated in FIG. 5.

In the illustration, two lunate magnetic elements 222a, 222b are placed in the lunate, the first element 222a for communicating with the scaphoid implant 200 in the same manner as the lunate magnetic element 222 described above and the second element 222b for communicating magnetically with the capitate implant 300. Also in FIG. 5, a hamate magnetic member 216 is affixed to the hamate 16 in a position to have a magnetic relationship with the capitate implant 300. A metacarpal magnetic implant 202 also is provided on the third metacarpal, for cooperating magnetically with the capitate implant 300 and an insert 203 is provided on the metacarpal magnetic implant 202. As illustrated, the magnetic elements 222a, 222b, and 216 are similar to magnetic elements described above, which are inserted into bore holes formed in the respective bone, and the metacarpal magnetic implant 202, is similar in composition to the implants 204, 211. This alternative embodiment is not limited to these arrangements. Generally speaking, the specifics of the type, size, and placement of the magnetic implants will be dictated by the procedures undertaken to remove diseased areas from surrounding bones.

Like in previous embodiments, in the embodiment of FIG. 5 other bones and structure in the joint are not affected by the prosthesis. So, for example, native structure is left intact where possible, while diseased surfaces and bones are repaired. The magnetic relationships between the magnetic implants, the scaphoid implant, and the capitate implant act to provide proper orientation of the components, essentially serving as "magnetic ligaments." The overall result is a reconstructed wrist with operation that very closely approximates pre-injury operation.

As should be appreciated by those having ordinary skill in the art, other or additional bones in the wrist could also be replaced with a similar implant, for example, because the disease has further progressed.

Although the invention has been described in terms of replacing a wrist, it may be used in other instances. Specifically, the novel concepts described herein may be used in other instance of complex joints that include more than three bones that move relatively.

Figure 6:
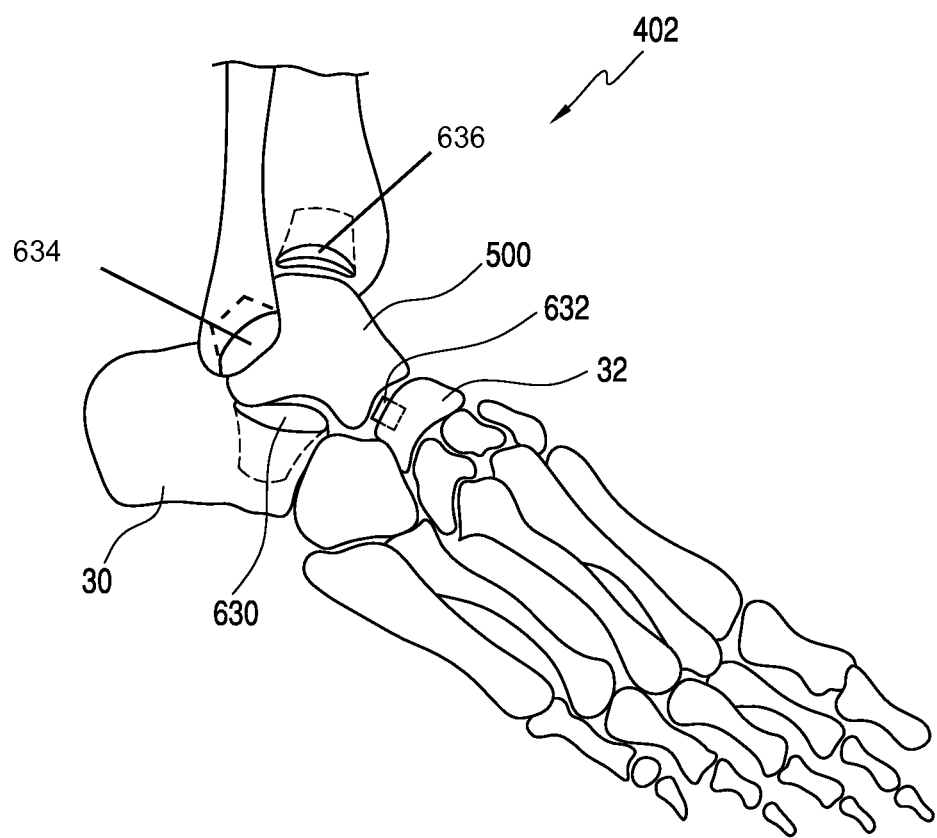
FIG. 6 is a perspective view of a preferred embodiment of concepts of the invention used to repair an ankle

For example, FIG. 6 illustrates a foot 402 in which the talus has been replaced with a talus implant 500. Like in the embodiments described above, surfaces of the navicular, the tibia and fibula, and/or the calcaneus may be freed from arthritis or other disease and fitted with a magnetic implant that cooperates with the talus implant to recreate anatomy prior to the injury. In FIG. 6, a calcaneus magnetic implant 630 is provided in the calcaneus 30 and a navicular magnetic element 632 is provided in the navicular 32. As will be appreciated, other or additional bones also may include magnetic elements, and the invention is not limited to the magnetic elements illustrated. For example FIG. 6 also illustrates a fibular magnetic element 634 and a tibial magnetic element 636. Those elements are disposed at the distal end of the fibula and tibia, and are similar in construction and application to the radial magnetic element 204 shown in FIG. 3, disposed in the radius. Although not illustrated, an insert may be disposed on each of the fibular and tibial magnetic elements 634, 636. In other embodiments, other bones may be replaced with an implant. Moreover, the invention is not limited to the illustrated magnetic attachments; any of the magnetic attachments described in the disclosure can be used to hold the talus implant 500 in place. As should be appreciated, the invention is particularly useful in complex joints like the wrist, ankle and foot, where the joint comprises a plurality of bones, and those bones move relative to each other.

The invention also is not limited to application in humans. Those having ordinary skill in the art will appreciate many additional applications, such as in animal applications.

While the invention has been described in connection with several presently preferred embodiments thereof, those skilled in the art will appreciate that many modifications and changes may be made without departing from the true spirit and scope of the invention which accordingly is intended to be defined solely by the appended claims.

The invention claimed is:

1. A wrist prosthesis comprising:
a magnetic implant approximating the size of a bone to be replaced;
a first magnetic bone implant securable to a first bone adjacent the bone to be replaced; and
a second magnetic bone implant securable to a second bone adjacent the bone to be replaced,
wherein each of the first and second magnetic bone implants have a magnetic relationship with the magnetic implant,
wherein the magnetic implant is a scaphoid implant approximating the size and shape of a scaphoid to be removed from a patient's wrist, the first magnetic bone implant is securable to a first bone adjacent the scaphoid to be replaced, and the second magnetic bone implant is securable to a second bone adjacent the scaphoid to be replaced, wherein the first and second magnetic bone implants each have a magnetic relationship with the scaphoid implant,
wherein at least one of the scaphoid implant or the first and second magnetic bone implants comprise a magnet, and wherein the first bone and the second bone are selected from the trapezium, the trapezoid, the lunate, the capitate, and the radius.

2. The prosthesis of claim 1, wherein the scaphoid implant comprises a magnet.

3. The prosthesis of claim 1, wherein at least one of the first magnetic bone implant and the second magnetic bone implant comprise a magnet.

4. The prosthesis of claim 1 wherein the first magnetic bone implant comprises a first magnet, the second magnetic bone implant comprises a second magnet and further comprising one or more additional magnets, the one or more additional magnets being securable to additional bones adjacent the scaphoid to be replaced.

5. The prosthesis of claim 4, wherein the first, second, and one or more additional magnets are securable to the trapezium, the trapezoid, the lunate, the capitate or the radius.

6. The prosthesis of claim 1, wherein at least one of the first magnetic bone implant and the second magnetic bone implant comprises a magnetic element and an insert disposed on the magnetic element, the scaphoid implant contacting the insert.

7. The prosthesis of claim 6, wherein the insert is a biocompatible material with a low coefficient of friction.

8. The prosthesis of claim 6, wherein the insert is made of one of polyethylene, ceramic, and pyrolytic carbon.

9. The prosthesis of claim 1, further comprising a shield disposed on at least one of the scaphoid implant, the first magnetic bone implant, and the second magnetic bone implant.

10. The prosthesis of claim 1, wherein the scaphoid implant comprises a magnet and at least one of the first magnetic bone implant and the second magnetic bone implant is attracted to the magnet.

11. The prosthesis of claim 1, wherein at least one of the first magnetic bone implant and the second magnetic bone implant is attracted to the scaphoid implant.

12. The prosthesis of claim 1, wherein each of the scaphoid implant and the first and second magnetic bone implants comprise magnets.

\* \* \* \* \*